United States Patent [19]

Soto et al.

[11] Patent Number: 4,550,116
[45] Date of Patent: Oct. 29, 1985

[54] PIPERIDINE DERIVATIVES

[75] Inventors: Jose M. P. Soto; Armando V. Noverola; Jacinto M. Mauri, all of Barcelona; Robert G. W. Spickett; Tibadabo, all of Spain

[73] Assignee: Fordonal, S.A., Madrid, Spain

[21] Appl. No.: 633,958

[22] Filed: Jul. 24, 1984

[30] Foreign Application Priority Data

Aug. 5, 1983 [GB] United Kingdom ................. 8321157

[51] Int. Cl.$^4$ ................. A61K 31/445; C07D 211/46; C07D 409/04
[52] U.S. Cl. ..................... 514/327; 514/326; 546/213; 546/216; 546/221
[58] Field of Search ....................... 546/213, 221, 216; 514/326, 327

[56] References Cited

U.S. PATENT DOCUMENTS

| 2,716,122 | 8/1955 | Levy et al. | 546/216 |
| 3,080,372 | 3/1963 | Janssen et al. | 546/213 |
| 3,122,555 | 2/1964 | Janssen et al. | 546/213 |
| 3,438,991 | 4/1969 | Janssen et al. | 546/221 |
| 3,446,014 | 2/1972 | Bader et al. | 546/216 |
| 3,462,444 | 8/1969 | Beckett et al. | 546/221 |
| 3,679,666 | 7/1972 | Malatestinic et al. | 546/221 |
| 3,743,645 | 7/1973 | Helsley et al. | 546/221 |
| 3,799,932 | 3/1974 | Yamamoto et al. | 546/221 |
| 4,070,473 | 1/1978 | Hernestam et al. | 546/216 |
| 4,075,346 | 2/1978 | Sasajima et al. | 546/221 |
| 4,216,218 | 8/1980 | Klioze et al. | 546/216 |
| 4,312,876 | 1/1982 | Klioze et al. | 546/216 |
| 4,424,357 | 1/1984 | Klioze et al. | 546/216 |

Primary Examiner—Robert T. Bond
Attorney, Agent, or Firm—Lyon & Lyon

[57] ABSTRACT

Compounds of the general formula I:

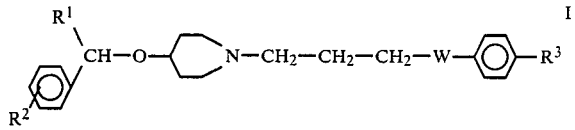

wherein $R^1$ represents a thienyl group, or a phenyl group optionally substituted by a halogen (preferably fluorine or chlorine) atom, a lower alkoxy or lower alkyl group, $R^2$ represents a hydrogen or halogen (preferably fluorine) atom, a lower alkoxy or lower alkyl group, $R^3$ represents a hydrogen or halogen (preferably fluorine) atom, a lower alkylthio, lower alkoxy or lower alkyl group, or a cycloalkyl group containing 5 or 6 carbon atoms, or a group of the general formula:

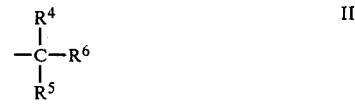

wherein $R^4$ and $R^5$ singly each represents a hydrogen atom or lower alkyl group, $R^6$ represents a cycloalkyl, hydroxymethyl, carboxy or lower alkoxycarbonyl group, and W represents a carbonyl

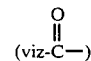

or a hydroxymethylene [viz. —CH(OH)—] group, and pharmacologically acceptable salts thereof possess potent selective Histamine $H_1$-receptor blocking and calcium antagonist properties and are of interest in the treatment of a variety of respiratory, allergenic and cardiovascular disease states. The new compounds can be prepared by various methods based on the condensation of α-substituted benzyl halides with N-(benzoylpropyl or phenyl-hydroxypropyl)-4-hydroxy piperidines or condensation of di-substituted-methoxy-piperidines with a benzoylpropyl halide or a phenyl-hydroxypropyl-halide followed, where necessary, by removal of protecting groups.

10 Claims, No Drawings

PIPERIDINE DERIVATIVES

DESCRIPTION

This invention relates to new therapeutically useful piperidine derivatives, to processes for their preparation and pharmaceutical compositions containing them.

The new piperidine derivatives of the present invention are those compounds of the general formula:

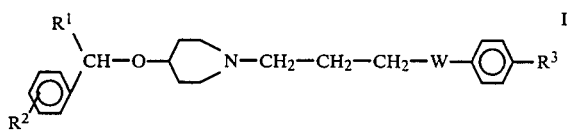

wherein $R^1$ represents a thienyl group, or a phenyl group optionally substituted by a halogen (preferably fluorine or chlorine) atom, a lower alkoxy or lower alkyl group, $R^2$ represents a hydrogen or halogen (preferably fluorine) atom, a lower alkoxy or lower alkyl group, $R^3$ represents a hydrogen or halogen (preferably fluorine) atom, a lower alkylthio, lower alkoxy or lower alkyl group, or a cycloalkyl group containing 5 or 6 carbon atoms, or a group of the general formula:

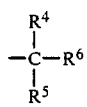

wherein $R^4$ and $R^5$ singly each represents a hydrogen atom or lower alkyl group, $R^6$ represents a cycloalkyl, hydroxymethyl, carboxy or lower alkoxycarbonyl group, and W represents a carbonyl

or a hydroxymethylene [viz—CH(OH)—] group, and pharmacologically acceptable salts, e.g. acid addition salts, thereof.

The qualification "lower" as applied herein to alkylthio, alkyl and alkoxy groups mean that the group in question contains at most 6 (and preferably not more than 4) carbon atoms. Preferred examples of cycloalkyl groups within the definition of symbol $R^6$ are cyclopropyl, cyclopentyl and cyclohexyl.

Of the piperidine derivatives of general formula I those wherein $R^1$ represents a thienyl group or a phenyl group optionally substituted by a halogen atom, $R^2$ represents a hydrogen or halogen atom, and $R^3$ represents a cyclohexyl or a lower alkyl (preferably isopropyl or tert-butyl) group, are of particular importance. When $R^3$ represents a group of general formula II, those compounds wherein $R^4$ and $R^5$ each represent a methyl group and $R^6$ represents a carboxy group, are preferred. Preferably the said halogen atom is fluorine or chlorine. Presently preferred compounds are 4-diphenylmethoxy-1-[3-(4-tert-butylbenzoyl)propyl]-piperidine, 4-diphenylmethoxy-α-(4-tert-butylphenyl)-1-piperidinebutanol, 4-di-(4-fluorophenyl)methoxy-1-[3-(4-tert-butylbenzoyl)propyl]-piperidine, 4-[α-(2-thienyl)-benzyloxy]-1-[3-(4-tert-butylbenzoyl)propyl]-piperidine, 4-diphenylmethoxy-α-(4-cyclohexylphenyl)-1-piperidine butanol and 4-diphenylmethoxy-1-[3-(4-isopropylbenzoyl)-propyl]-piperidine.

According to a feature of the present invention, the piperidine derivatives of general formula I except for those compounds wherein $R^3$ represents a group of formula II in which $R^6$ represents a hydroxymethyl or carboxy group, viz the piperidine derivatives of the general formula:

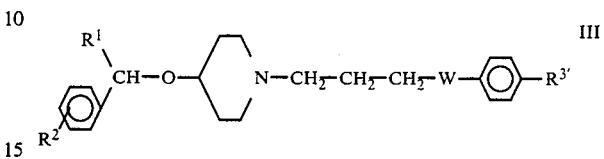

(wherein $R^1$, $R^2$ and W are as hereinbefore defined, and $R^{3'}$ represents a hydrogen or halogen atom, a lower alkylthio, lower alkoxy or lower alkyl group, or a cycloalkyl group containing 5 or 6 carbon atoms, or a group of formula II hereinbefore depicted wherein $R^4$ and $R^5$ are as hereinbefore defined and $R^6$ represents a cycloalkyl or lower alkoxycarbonyl group) are prepared by the process which comprises reacting a halide of the general formula:

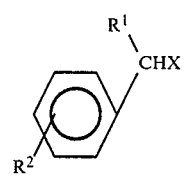

(wherein $R^1$ and $R^2$ are as hereinbefore defined, and X represents a chlorine or bromine atom) with an N-substituted-4-hydroxypiperidine of the general formula:

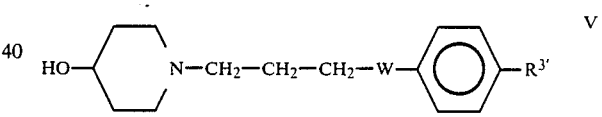

wherein W and $R^{3'}$ are as hereinbefore defined.

The reaction is preferably carried out in an inert organic solvent, for example, toluene, xylene, dioxan, methyl isobutyl ketone or N,N-dimethylformamide, at a temperature between 80° and 140° C. and in the presence of an acid-binding agent such as an alkali metal carbonate or bicarbonate.

The halide starting materials of general formula IV are obtained by methods known per se, for example by reaction of a hydroxy compound of the general formula:

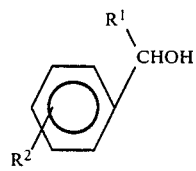

(wherein $R^1$ and $R^2$ are as hereinbefore defined) with a phosphorous or thionyl chloride or bromide in an inert organic solvent.

The N-substituted-4-hydroxypiperidine starting materials of general formula V are preferably prepared by condensation of 4-hydroxypiperidine with a halide of the general formula:

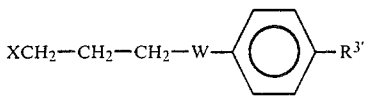

VII (wherein W, $R^{3'}$ and X are as hereinbefore defined) in an organic solvent, such as toluene, dioxan, xylene or methyl isobutyl ketone or N,N-dimethylformamide, at a temperature between 80° and 140° C. and in the presence of an acid-binding agent such as an alkali metal carbonate or bicarbonate.

The piperidine derivatives of general formula I except for those compounds wherein $R^3$ represents a group of formula II in which $R^6$ represents a hydroxymethyl or carboxy group (viz. the piperidine derivatives of general formula III) are also prepared, according to another feature of the invention, by the reaction of a phenylmethoxy-piperidine derivative of the general formula:

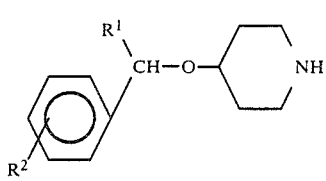

VIII (wherein $R^1$ and $R^2$ are as hereinbefore defined) with a halide of general formula VII.

The reaction is preferably carried out in an organic solvent, for example, toluene, dioxan, xylene, methyl isobutyl ketone or N,N-dimethyl-formamide, at a temperature between 80° and 140° C. and in the presence of an acid-binding agent such as an alkali metal carbonate or bicarbonate.

The phenylmethoxy-piperidine derivative starting materials of general formula VIII can be prepared by condensation of a halide of general formula IV with 1-ethoxycarbonyl-4-hydroxypiperidine under the same conditions previously described for the preparation of piperidine derivatives of general formula I by the reaction of compounds of general formulae IV and V, and the resulting intermediate compound of the general formula:

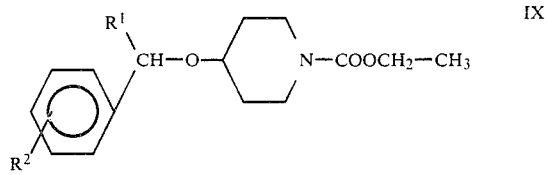

IX (wherein $R^1$ and $R^2$ are as hereinbefore defined) is hydrolyzed with sodium or potassium hydroxide in an organic solvent, for example ethanol or isopropanol, at the boiling point of the solvent.

The piperidine derivatives of general formula I wherein $R^1$, $R^2$ and W are as hereinbefore defined and $R^3$ represents a group of formula II in which $R^6$ represents a carboxy group, viz compounds of the general formula:

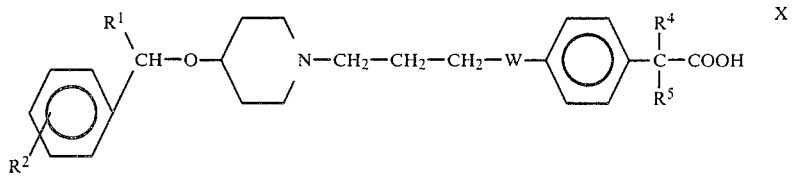

X (wherein $R^1$, $R^2$, $R^4$, $R^5$ and W are as hereinbefore defined) are prepared, according to a feature of the invention, from the corresponding alkyl esters of the general formula:

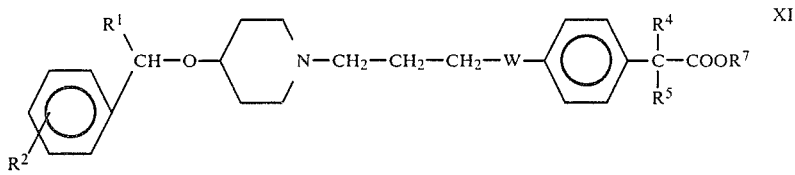

XI (wherein $R^7$ represents a lower alkyl group, and the other symbols are as hereinbefore defined) by hydrolysis, for example by reaction with sodium or potassium hydroxide, or hydrochloric or sulphuric acid, in an inert organic solvent, such as methanol or ethanol, or water at a temperature between 20° C. and the boiling point of the solvent.

The starting materials of general formula XI can be prepared by the reaction of a compound of general formula IV with a compound of general formula V wherein $R^{3'}$ represents a group of the formula:

XII wherein $R^4$, $R^5$ and $R^7$ are as hereinbefore defined.

According to another feature of the invention, the piperidine derivatives of general formula I wherein $R^1$ and $R^2$ are as hereinbefore defined, $R^3$ represents a group of formula II in which $R^6$ represents a hydroxymethyl group, and W represents a carbonyl group, viz the piperidine derivatives of the general formula:

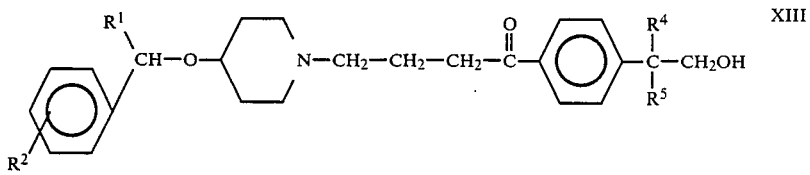

(wherein the various symbols are as hereinbefore defined) are prepared by reducing the carboxy or alkoxycarbonyl group of a corresponding compound in which the carbonyl group is protected as an ethylene ketal and conforming to the general formula:

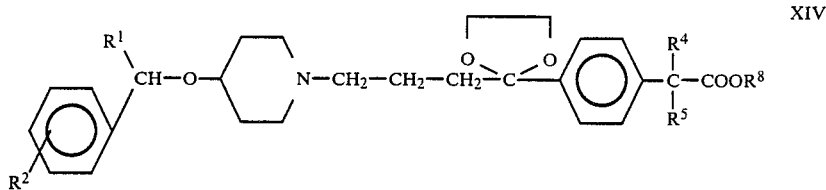

(wherein R¹, R², R⁴ and R⁵ are as hereinbefore defined, and R⁸ represents a hydrogen atom or an alkyl group, preferably a lower alkyl group) to a hydroxymethyl group, and subjecting the resulting hydroxymethyl derivative of the general formula:

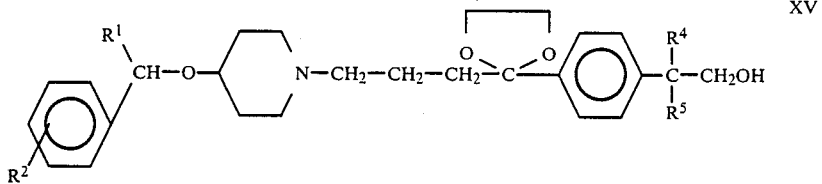

(wherein the various symbols are as hereinbefore defined) to acid hydrolysis to obtain a piperidine derivative of general formula XIII.

The reduction of the carboxy or alkoxycarbonyl group of the compounds of general formula XIV is preferably carried out with diborane or lithium aluminum hydride in an inert organic solvent, such as diethyl ether, diisopropyl ether, tetrahydrofuran or dioxan, at a temperature between 20° and 80° C.

The acid hydrolysis of the compounds of general formula XV is preferably carried out with hydrochloric or sulphuric acid in water, methanol or ethanol, at a temperature between 20° and the boiling point of the solvent.

The same acid hydrolsis process can be used to prepare the compounds of general formula I in which R³ represents a hydrogen or halogen atom, a lower alkylthio, lower alkoxy or lower alkyl group or a cycloalkyl group containing 5 or 6 carbon atoms and W represents a carbonyl group, viz the piperidine derivatives of the general formula:

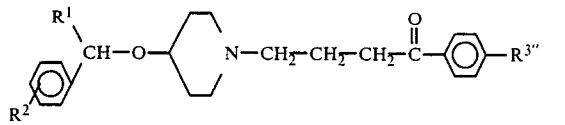

wherein R¹ and R² are as hereinbefore defined and R³" represents a hydrogen or halogen atom, a lower alkylthio, lower alkoxy or lower alkyl group or a cycloalkyl group containing 5 or 6 carbon atoms.

In this case the acid hydrolysis is carried out starting from the corresponding dioxolane derivatives of formula:

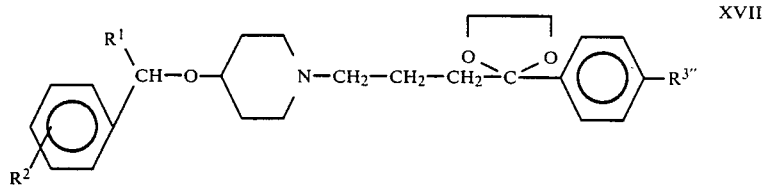

(wherein the various symbols are as hereinbefore defined) under the same conditions disclosed for compounds of general formula XV.

The piperidine derivatives of general formula I wherein R¹ and R² are as hereinbefore defined, R³ represents a group of formula II in which R⁶ represents a hydroxymethyl group, and W represents a hydroxymethylene group, are prepared by reducing the carboxy or alkoxycarbonyl group of a corresponding compound of the general formula:

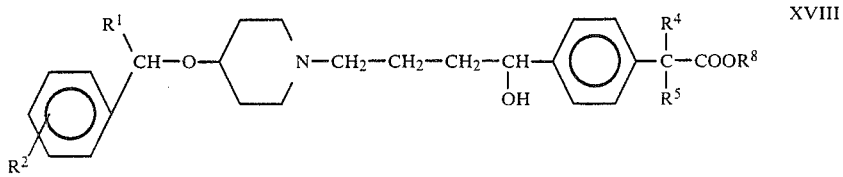

(wherein the various symbols are as hereinbefore defined) to a hydroxymethyl group.

The same piperidine derivatives of general formula I (as mentioned in the preceding paragraph) can also be prepared by reducing the carboxy or alkoxycarbonyl group, and the carbonyl group, of a compound of the general formula:

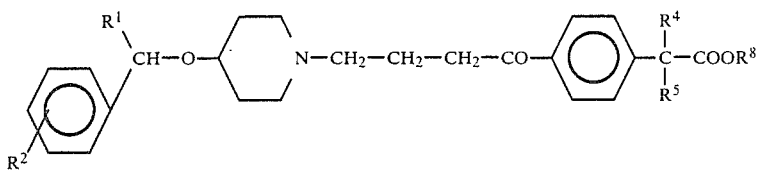

wherein $R^1$, $R^2$, $R^4$, $R^5$ and $R^8$ are as hereinbefore defined. In this case the carbonyl and —$COOR^8$ groups are reduced concomitantly to hydroxymethylene and hydroxymethyl respectively.

The reduction of the starting materials of general formula XVIII or XIX can be effected using the same means and reaction conditions previously described for the reduction of compounds of general formula XIV.

The piperidine derivatives of general formula I, wherein $R^1$, $R^2$ and $R^3$ are as defined in relation to that formula and W represents a hydroxymethylene group, are prepared, according to another feature of the invention, by the reduction of the carbonyl group of a corresponding compound of general formula I, wherein W is a carbonyl group, to a hydroxymethylene group. The reduction is advantageously carried out with sodium borohydride in an inert organic solvent, such as methanol or ethanol, at a temperature between 20° C. and the boiling point of the solvent.

The piperidine derivatives of general formula I can be converted by methods known per se into acid addition salts, for example by reaction of the basic compounds with acids in appropriate solvents, for example alcohols, ethers or chlorinated hydrocarbons. Suitable acid addition salts are those derived from inorganic acids, for example the hydrochlorides and sulphates, and organic acids, for example, the fumarates, acetates, succinates and citrates.

The piperidine derivatives of general formula I wherein $R^3$ represents a group of formula II and $R^6$ therein represents a carboxy group may also form pharmacologically-acceptable salts with alkali or alkaline earth metals, which salts are formed by reaction of the said acid derivatives of general formula I with an alkali metal or alkaline earth metal carbonate or hydroxide using water, methanol or ethanol, as solvent at a temperature between 20° and 80° C.

The piperidine derivatives of general formula I possess potent selective histamine $H_1$—receptor blocking and calcium antagonist properties and should prove useful in the treatment of a variety of respiratory, allergic and cardiovascular disease states.

Thus, these compounds relax bronchial and vascular smooth muscle in vitro and in vivo and inhibit the constrictor influence of noradrenaline, potassium ions and various other agonist drugs. The compounds also inhibit responses of intestinal and tracheal preparations to histamine, acetylcholine and barium chloride and block the bronchoconstruction induced by histamine aerosol in guinea-pigs in doses less than 1 mg/kg animal body weight administered orally. They also possess antianaphylactic properties in the rat, inhibit the skin lesions to a variety of anaphylactic mediators (histamine, 5-hydroxytryptamine, bradykinin, $LCD_4$, etc) and antagonize the Schultz-Dale response in the sensitized guinea-pig.

Quantitatively the piperidine derivatives of general formula I are more potent, and produce effects of greater duration, than cinnarizine and terfenadine in most tests and are active following parenteral an oral administration. Sedative and other actions upon the central nervous system are absent and the compounds are well tolerated with acute LD50 values in mice of over 1 g/kg animal body weight administered orally.

Experiments have been carried out with typical compounds of general formula I, viz.
4-diphenylmethoxy-1-[3-(4-tert-butylbenzoyl)propyl]-piperidine (compound 1),
4-diphenylmethoxy-1-[3-(4-isopropylbenzoyl)propyl]-piperidine (compound 2),
4-diphenylmethoxy-1-[3-(4-ethylbenzoyl)propyl]-piperidine (compound 3),
4-diphenylmethoxy-1-[3-(4-cyclopropylmethylbenzoyl)propyl]-piperidine (compound 4),
4-[α-(2-thienyl)benzyloxy]-1-[3-(4-tert-butylbenzoyl)propyl]-piperidine (compound 5),
4-diphenylmethoxy-α-(4-cyclohexylphenyl)-1-piperidinebutanol (compound 6),
4-di(4-fluorophenyl)methoxy-1-[3-(4-tert-butylbenzoyl)propyl]-piperidine (compound 7) and
4-diphenylmethoxy-α-(4-tert-butylphenyl)-1-piperidinebutanol (compound 8),
to compare inter alia such pharmacological activities with that of the drugs known as cinnarizine, i.e. $N^1$-benzhydryl-$N^4$-cinnamylpiperazine and terfenadine, i.e. α-[4-(1,1-dimethylethyl)phenyl]-4-(hydroxydiphenylmethyl)-1-piperidinebutanol.

The experiments with usual test animals were conducted and evaluated in the following manner:

A Rat hindquarter preparation

Responses of rat hindquarters perfused at constant rate were elicited by high $-K^+$ (80 mM) Krebs' solution. Test compounds ($10^{-7}$M) were perfused for 20 minutes and then compound-free Krebs' perfusion was resumed for 40 min. Results show the maximum percentage inhibition produced by the compounds and the percentage recovery of response at 1 h following perfusion with normal Krebs' solution.

B. Antihistamine activity in anaesthetized rats

Test compounds were administered to pentobarbitone anaesthetized rats at 0.3 mg/kg i.v. following stable, submaximal, vasodepressor responses to histamine. Results were calculated in terms of percentage inhibition of the histamine response: $+ = 10-25\%$, $++ = 25-50\%$ and $+++ = 50-75\%$ $++++ = 75-100\%$ inhibition.

C. Histamine aerosol

The number of guinea-pigs (groups of 5) protected from a 5 minute challenge of nebulized histamine 1 hour after oral dosing with the compounds at 0.3 mg/kg was noted and expressed: $+ = 10-25\%$, $++ = 25-50\%$ and $+++ > 50\%$ protection.

D. Protection against a lethal dose of adrenaline

Groups of 10 ♂ swiss mice ($25 \pm 3$ g) were pretreated orally with compounds (100 mg/kg) suspended in carboxymethyl cellulose 1 h before receiving an intraveneous injection of 2 mg/kg adrenaline. The number of animals surviving 15 min later was noted and expressed as a percentage.

E. Acute toxicity

Acute toxicity was assessed in groups of 3 mice given the test compounds suspended in 1% carboxymethylcellulose at 30, 100, 300 and 1000 mg/kg orally. The number of deaths occurring in the ensuing 48 hour period was recorded and approximate $LD_{50}$ values noted in terms of an $LD_{50}$ dose-range.

The results of the experiments are tabulated below.

In general these new piperidine derivatives will be of use in cases of allergy, rhinitis asthma etc. where the use of non-sedative antihistamines and compounds inhibiting the release of and/or the end-organ responses to the chemical mediators liberated from, for example mast cells, during the allergic response is indicated. On the other hand because of their potent vascular activity the new piperidine derivatives will also be useful in the treatment of cerebral or peripheral vascular insufficiency and certain types of migraine and vertigo.

Also included within the scope of the present invention are pharmaceutical compositions which comprise, as active ingredient, at least one piperidine derivative of general formula I, or a pharmacologically-acceptable salt thereof, in association with a pharmaceutically-acceptable carrier or diluent. Preferably the compositions are made up in a form suitable for oral, rectal or parenteral administration.

The pharmaceutically-acceptable carriers or diluents which are admixed with the active compound or compounds, or salts thereof, to form the compositions of this invention are well-known per se and the actual excipients used depend inter alia on the intended method of administration of the compositions.

Compositions of this invention are preferably adapted for administration per os. In this case, the compositions for oral administration may take the form of tablets, capsules, lozenges or effervescent granules or liquid preparations such as elixirs, syrups or suspensions, all containing one or more compounds of the invention; such preparations may be made by methods well known in the art.

The diluents which may be used in the preparations of the compositions include those liquid and solid diluents which are compatible with the active ingredient, together with colouring or flavouring agents, if desired. Tablets or capsules may conveniently contain between 1 and 100 mg, preferably from 5 to 50 mg, of active ingredient or the equivalent amount of a pharmacologi-

TABLE 1

| COMPOUND | TEST A RAT HINDQUARTERS | | TEST B ANTIHISTAMINE IN RAT | TEST C ANTIHISTAMINE AEROSOL | TEST D ANTI-ADRENALINE | TEST E ACUTE TOXICITY |
|---|---|---|---|---|---|---|
| | % Inhibition | % Recovery | | | | |
| CINNARIZINE | 61 | 100 | +++ | + | 40 | >1000 |
| TERFENADINE | 44 | 100 | ++ | + | 20 | >1000 |
| 1 | 70 | 56 | ++++ | +++ | 50 | >1000 |
| 2 | 59 | 50 | +++ | | 50 | >1000 |
| 3 | 65 | 50 | +++ | | 20 | |
| 4 | 75 | 40 | ++ | | 40 | |
| 5 | 65 | 40 | +++ | | | |
| 6 | 57 | 55 | ++ | | 20 | |
| 7 | 62 | 13 | +++ | | 40 | |
| 8 | 69 | 58 | ++ | ++ | 60 | |

As will be seen from the results of the experiments summarized in Table 1, the piperidine derivatives of general formula I in vitro, in the rat hindquarter preparation produced anti-vasoconstrictor effects which were much longer lasting than those of terfenadine and cinnarizine. Note especially compounds 1,5,4,3, and 7. In compound 1 potent, directly acting anti-vasoconstrictor activity is combined with extremely potent H1-histamine receptor antagonist properties both intraveously in rats and orally against histamine aerosol in guinea-pigs and had a relatively low oral toxicity in the mouse. Anticholinergic, sedative and other CNS side effects are not apparent with these new piperidine derivatives even at high doses.

cally-acceptable salt thereof. The compounds may also be incorporated into pellets coated with appropriate natural or synthetic polymers known in the art to produce sustained release characteristics or incorporated with polymers into tablet form to produce the same characteristics.

The liquid compositions adapted for oral use may be in the form of solutions or suspensions. The solutions may be aqueous solutions of an acid addition salt of the piperidine derivative in association with, for example, sucrose or sorbitol to form a syrup. The suspensions may comprise an insoluble or microencapsulated form of an active compound of the invention in association with water of other pharmaceutically-acceptable liquid medium together with a suspending agent or flavouring agent.

Compositions for parenteral injection may be prepared from soluble acid addition salts of the piperidine derivative, which may or may not be freeze-dried and which may be dissolved in water or an appropriate parenteral injectable fluid.

In human therapy, the doses of the compound of general formula I depend on the desired effect and duration of the treatment; adult doses are generally between 2 mg and 75 mg per day. In general, the physician will decide the posology taking into account the age and weight intrinsic to the patient being treated.

The following Examples illustrate the preparation of piperidine derivatives of the present invention.

EXAMPLE 1

(a) A mixture of 4-hydroxypiperidine (40.4 g.; 0.4 moles), p-tert-butyl-ω-chlorobutyrophenone, (105 g, 0.44 moles), sodium bicarbonate (67.2 g; 0.8 moles) and a crystal of potassium iodide in methyl isobutyl ketone (1 liter) was boiled under reflux for 24 hours. After cooling, the reaction mixture was washed with water, dried ($Na_2SO_4$) and the solvent removed in vacuo. The residue was salified with the stoichiometric amount of fumaric acid in a mixture of acetone and ethanol to give 1-[3-(4-tert-butylbenzoyl)propyl]-4-hydroxypiperidine fumarate (148 g), m.p. 163°–165° C. This compound was converted into the free base, and 1-[3-(4-tert-butylbenzoyl)propyl]-4-hydroxypiperidine was obtained and recrystallized from a mixture of diethyl ether and petroleum ether (b.p. 50°–70° C.). 102 g. were obtained (yield 84%), m.p. 63°–65° C.

(b) A mixture of 1-[3-(tert-butylbenzoyl)propyl]-4-hydroxypiperidine (60.68 g.; 0.2 moles) and sodium carbonate (42.4 g.; 0.4 moles) in methyl isobutyl ketone (500 ml) was heated to the boiling point and a solution of diphenylmethyl bromide (49.42 g.; 0.2 moles) in methyl isobutyl ketone (75 ml) was slowly added in 1.5 hours. The resulting mixture was boiled under reflux for another 12 hours, and then another solution of diphenylmethyl bromide (24.71 g.; 0.1 moles) in methyl isobutyl ketone (50 ml) was added and the mixture boiled under reflux again for 12 hours. Another solution of diphenylmethyl bromide in the same quantity was added and after refluxing for 12 additional hours the reaction mixture was cooled, washed with water, dried ($Na_2SO_4$) and the solvent removed in vacuo.

The residual oil was treated with the stoichiometric amount of fumaric acid in ethanol and 4-diphenylmethoxy-1-[3-(4-tert-butylbenzoyl)propyl]-piperidine fumarate crystallized. After recrystallisation from ethanol the pure compound was obtained (88 g.; yield 75%), m.p. 197°–198° C.

Also obtained in a similar manner to (b) above employing appropriate compounds of general formulae IV and V as starting materials were:

4-diphenylmethoxy-α-(4-tert-butylphenyl)-1-piperidinebutanol, m.p. 129°–131° C.

4-(α-phenyl-4-chlorobenzyloxy)-1-[3-(4-tert-butylbenzoyl)-propyl]-piperidine fumarate, m.p. 202°–204° C. (d);

4-di(4-fluorophenyl)methoxy-1-[3-(4-tert-butylbenzoyl)-propyl]-piperidine fumarate, m.p. 214°–216° C.;

4-diphenylmethoxy-1-[3-(4-isopropylbenzoyl)propyl]-piperidine fumarate, m.p. 155°–157° C.;

4-diphenylmethoxy-1-[3-(4-ethylbenzoyl)propyl]-piperidine fumarate, m.p. 145°–147° C.;

4-diphenylmethoxy-1-[3-(4-fluorobenzoyl)propyl]-piperidine fumarate, m.p. 159°–161° C.;

4-diphenylmethoxy-1-[3-(4-cyclohexylbenzoyl)propyl]-piperidine fumarate, m.p. 184°–186° C., 4-diphenylmethoxy-1-(3-benzoylpropyl)-piperidine fumarate m.p. 171°–173° C. (d).

bis[4-(α-phenyl-4-chlorobenzyloxy)-α-(4-tert-butylphenyl)-1-piperidinebutanol] fumarate, m.p. 185°–187° C.;

bis[4-di(4-fluorophenyl)methoxy)-α-(4-tert-butylphenyl)-1-piperidinebutanol] fumarate, m.p. 201°–203° C. (d);

bis[4-diphenylmethoxy-α-(4-isopropylphenyl)-1-piperidinebutanol] fumarate, m.p. 169°–171° C.;

4-diphenylmethoxy-α-(4-cyclohexylphenyl)-1-piperidinebutanol, m.p. 106°–108° C.;

4-diphenylmethoxy-α-phenyl-1-piperidinebutanol, m.p. 105°–107° C.;

4-diphenylmethoxy-α-(4-fluorophenyl)-1-piperidinebutanol, m.p. 91°–93° C.;

4-diphenylmethoxy-1-[3-(4-bromobenzoyl)propyl]-piperidine, m.p. 96°–98° C.;

4-diphenylmethoxy-α-(4-bromophenyl)-1-piperidinebutanol, m.p. 109°–111° C.;

4-diphenylmethoxy-1-[3-(4-cyclopropylmethylbenzoyl)propyl]-piperidine fumarate, m.p. 127°–129° C.;

4-diphenylmethoxy-1-[3-(4-methoxybenzoyl)propyl]-piperidine, m.p. 80°–82° C.;

4-diphenylmethoxy-α-(4-methoxyphenyl)-1-piperidinebutanol, m.p. 93°–95° C.;

4-diphenylmethoxy-1-[3-(4-isopropylthiobenzoyl)propyl]-piperidine fumarate m.p. 151°–153° C.;

4-di-(4-methoxyphenyl)methoxy-1-[3-(4-tert-butylbenzoyl)propyl]-piperidine fumarate, m.p. 184°–186° C.;

4-[α-(3-methylphenyl)-2-methylbenzyloxy]-1-[3-(4-tert-butylbenzoyl)propyl]-piperidine fumarate, m.p. 189°–191° C.;

4-[α-(2-thienyl)benzyloxy]-1-[3-(4-tert-butylbenzoyl)-propyl]-piperidine fumarate, m.p. 179°–181° C. (d);

4-di-(4-methoxyphenyl)methoxy-α-(4-tert-butylphenyl)-1-piperidine butanol, m.p. 118°–120° C.; and 4-[α-(3-methylphenyl)-2-methylbenzyloxy]-α-(4-tert-butylphenyl)-1-piperidine butanol, m.p. 108°–111° C.

EXAMPLE 2

(a) A solution of 1-ethoxycarbonyl-4-diphenylmethoxypiperidine (60 g; 0.176 moles) and 85% potassium hydroxide (116 g; 1.76 moles) in isopropanol (600 ml) was boiled under reflux for 6 hours. After cooling, concentrated hydrochloric acid was added until pH=2 and the solvent removed in vacuo. The resulting residue was dissolved in a small quantity of water, washed with diethyl ether and the aqueous solution was made alkaline with aqueous sodium hydroxide solution and extracted with methylene chloride. The organic solution was dried ($Na_2SO_4$), the solvent removed in vacuo and the residual oil treated with ethanolic hydrogen chloride solution. 4-Diphenylmethoxy-piperidine hydrochloride (38 g; yield 71%) was obtained.

(b) A mixture of 4-diphenylmethoxy-piperidine (44.5 g; 0.166 moles), p-tert-butyl-ω-chlorobutyrophenone (46. g; 0.195 moles) and sodium carbonate (20.6 g; 0.195 moles) in methyl isobutyl ketone (500 ml) was boiled under reflux for 48 hours. After cooling, the reaction mixture was washed with water, dried ($Na_2SO_4$) and the solvent removed in vacuo to give an oil which was dissolved in ethanol and salified with the stoichiometric amount of fumaric acid. After recrystallisation from ethanol, pure 4-diphenylmethoxy-1-[3-(4-tert-butylbenzoyl)propyl]piperidine fumarate (75 g; yield 77%) was obtained, m.p. 197°-198° C.

Also obtained in a similar manner to (b) above employing appropriate compounds of general formula VIII and VII as starting materials were:

4-di(4-fluorophenyl)methoxy-1-[3-(4-tert-butylbenzoyl)-propyl]-piperidine fumarate, m.p. 214°-216° C.;
4-diphenylmethoxy-1-[3-(4-fluorobenzoyl)propyl]-piperidine fumarate, m.p. 159°-161° C.;
4-diphenylmethoxy-1-[3-(4-isopropylbenzoyl)propyl]-piperidine fumarate, m.p. 155°-157° C.;
4-(α-phenyl-4-chlorobenzyloxy)-1-[3-(4-tert-butylbenzoyl)propyl]-piperidine fumarate, m.p. 202°-204° C. (d);
4-diphenylmethoxy-1-[3-(4-cyclohexylbenzoyl)propyl]-piperidine fumarate, m.p. 184°-186° C.;
4-diphenylmethoxy-1-(3-benzoylpropyl)-piperidine fumarate m.p. 171°-173° C. (d);
4-diphenylmethoxy-1-[3-(4-ethylbenzoyl)propyl]-piperidine fumarate, m.p. 145°-147° C.;
4-[α-(2-thienyl)benzyloxy]-1-[3-(4-tert-butylbenzoyl)-propyl]-piperidine fumarate, m.p. 179°-181° C. (d);
4-diphenylmethoxy-1-[3-(4-cyclopropylmethylbenzoyl)propyl]-piperidine fumarate, m.p. 127°-129° C.;
4-diphenylmethoxy-α-(4-cyclohexylphenyl)-1-piperidinebutanol, m.p. 106°-108° C.;
4-diphenylmethoxy-α-(4-tert-butylphenyl)-1-piperidinebutanol, m.p. 129°-131° C.;
bis[4-(α-phenyl-4-chlorobenzyloxy)-α-(4-tert-butylphenyl)-1-piperidine]butanol fumarate, m.p. 185°-187° C.;
4-diphenylmethoxy-1-[3-(4-bromobenzoyl)propyl]-piperidine, m.p. 96°-98° C.;
4-diphenylmethoxy-1-[3-(4-methoxybenzoyl)propyl]-piperidine, m.p. 80°-82° C.
4-diphenylmethoxy-α-(4-fluorphenyl)-1-piperidinebutanol, m.p. 91°-93° C.;
4-diphenylmethoxy-α-phenyl-1-piperidinebutanol, m.p. 105°-107° C.;
4-diphenylmethoxy-1-[3-(4-isopropylthiobenzoyl)-propyl]piperidine fumarate, m.p. 151°-153° C.;
4-di-(4-methoxyphenyl)methoxy-1-[3-(4-tert-butylbenzoyl)propyl]-piperidine fumarate, m.p. 184°-186° C.;
bis[4-di(4-fluorphenyl)methoxy]-α-(4-tert-butylphenyl)-1-piperidine butanol fumarate, m.p. 201°-203° C. (d);
4-[α-(3l -methylphenyl)-2-methylbenzyloxy]-1-[3-(4-tert-butylbenzoyl)propyl]-piperidine fumarate, m.p. 189°-191° C.

EXAMPLE 3

To a solution of 4-diphenylmethoxy-1[3-(4-tert-butylbenzoyl)propyl]-piperidine (4.7 g; 0.01 mol) in ethanol (80 ml), sodium borohydride (0.4 g; 0.0105 moles) was added, and the mixture was boiled under reflux for 1.5 hours. Then the solvent was removed in vacuo and the residue dissolved in methylene chloride. The resulting solution was washed with water, dried (Na₂SO₄) and the solvent removed in vacuo to give an oil, which was crystallized on treatment with petroleum ether (b.p. 50°-70° C.). 4-Diphenylmethoxy-α(-4-tert-butylphenyl)-1-piperidinebutanol (3.8 g; yield 80.6%) was obtained, m.p. 129°-131° C.

Also obtained in a similar manner were:
4-diphenylmethoxy-α-(4-cyclohexylphenyl)-1-piperidinebutanol m.p. 106°-108° C.;
4-diphenylmethoxy-α-phenyl-1-piperdinebutanol, m.p. 105°-107° C.;
4-diphenylmethoxy-α-(4-methoxyphenyl)-1-piperidinebutanol, m.p. 93°-95° C.;
4-diphenylmethoxy-α(4-bromophenyl)-1-piperidinebutanol, m.p. 109°-111° C.;
4-diphenylmethoxy-α-(4-fluorphenyl)-1-piperidinebutanol, m.p. 91°-93° C.;
bis[4-diphenylmethoxy-α-(4-isopropylphenyl)-1-piperidinebutanol] fumarate, m.p. 169°-171° C.;
bis[4-di(4-fluorophenyl)methoxy)-α-(4-tert-butyphenyl)-1-piperidine butanol] fumarate, m.p. 201°-203° C. (d);
bis[4-(α-phenyl-4-chlorobenzyloxy)-α-(4-tert-butylphenyl)-1-piperidine butanol] fumarate, m.p. 185°-187° C.;
4-di-(4-methoxyphenyl)methoxy-α-(4-tert-butylphenyl)-1-piperidine butanol, m.p. 118°-120° C.;
4-[α-(3-methylphenyl)-2-methylbenzyloxy]-α-(4-tert-butylphenyl)-1-piperidine butanol, m.p. 108°-110° C. and
4-diphenylmethoxy-α-(4-ethylphenyl)-1-piperidinebutanol, m.p. 103°-105° C.

EXAMPLE 4

A solution of 4-diphenylmethoxy-1-[3-[2-(4-tert-butylphenyl)-1,3-dioxolan-2-yl]propyl]piperidine (10.3 g; 0.02 mols), prepared as described in Example 2, in 2N hydrochloric acid aqueous solution (50 ml) and ethanol (50 ml) was stirred at room temperature for 24 hours after which the mixture was alkalinized with sodium hydroxide aqueous solution. The ethanol was removed in vacuo and the insoluble solid collected by filtration and dried when 4-diphenylmethoxy-1[3-(4 tert-butylbenzoyl)propyl]-piperidine (8.2 g; 87.3%) was obtained; m.p. 84°-86° C. after recrytallisation from diethyl ether.

Also obtained in a similar manner employing 4-di(4-fluorophenyl)methoxy-1-[3-[2-(4-tert-butylphenyl)-1,3-dioxolan-2-yl]propyl]piperidine (m.p. of fumarate 227°-229° C. (d)) as starting material, was: 4-di(4-fluorphenyl)methoxy-1-[3-(4-tert-butylbenzoyl)propyl]-piperidine, m.p. of fumarate, 214°-216° C.

EXAMPLE 5

(a) To a mixture of ethyl 4-[4-(4-hydroxypiperid-1-yl)butyroyl]α,α-dimethylphenylacetate (18 g; 0.05 moles) and sodium carbonate (10.6 g; 0.1 mol) in methyl isobutyl ketone (100 ml), a solution of diphenylmethyl bromide (12 g; 0.05 moles) in methyl isobutyl ketone (50 ml) was slowly added and the resulting mixture boiled under reflux for 12 hours. Then another solution of diphenylmethyl bromide (6 g; 0.025 moles) in methyl isobutyl ketone (15 ml) was added and the mixture boiled under reflux again for 24 hours. The reaction mixture was cooled, washed with water, the solvent removed in vacuo and the residue treated with the stoichiometric amount of fumaric acid in ethanol. The obtained solid was recrystallized from methyl ethyl ketone and from ethanol to give ethyl 4-[4-(4-diphenylmethoxypiperid-1-yl)butyroyl]α,α-dimethylphenylacetate fumarate (5.6 g; yield 17.4%) which melts at 168°-170° C.

(b) A mixture of ethyl 4-[4-(4-diphenylmethoxypiperid-1-yl)butyroyl]α,α-dimethylphenylacetate (5.4 g; 0.0102 moles), 1N sodium hydroxide aqueous solution (15 ml) and ethanol (15 ml) was boiled under reflux for 4 hours, the ethanol removed in vacuo and the resulting aqueous solution diluted with water and neutralized with 1N hydrochloric acid aqueous solution. The solvent was removed in vacuo, the residue treated with anhydrous ethanol and the insoluble sodium chloride filtered off. The solution was evaporated to dryness and after repeating the treatment to eliminate the sodium chloride, 3 g of an oil were obtained which solidifies on treatment with diisopropyl ether. 4-[4-(4-diphenylmethoxypiperid-1-yl)butyroyl]α,α-dimethylphenylacetic acid was obtained (yield 58.9%) m.p. 93°–95° C.

EXAMPLE 6

A solution of ethyl 4-[4-(4-diphenylmethoxypiperid-1-yl)butyroyl]αα-dimethylphenylacetate prepared as described in Example 5-a (5.2 g; 0.01 mol) in anhydrous diethyl ether (15 ml) was slowly added to a suspension of lithium aluminium hydride (1.52 g; 0.04 moles) in anhydrous diethyl ether (60 ml). The reaction mixture was boiled under reflux for 1 hour and, after cooling, water (1.5 ml) 4N sodium hydroxide aqueous solution (1.5 ml) and water (4.5 ml) were succesively added. The white precipitate was filtered off, the organic solution dried ($Na_2SO_4$) and the solvent removed in vacuo. The obtained residue was solved in acetone and purified by column chromatography using silica gel-60 Merck, Darmstadt. Pure 4-diphenylmethoxy-60 -[4-(1,1-dimethyl-2-hydroxyethyl)phenyl]-1-piperidinebutanol (yield 52.4%) was obtained, m.p. 122°–124° C.

EXAMPLE 7

1000 bottles (150 ml volume) each containing a solution of 750 mg of 4-diphenylmethoxy-1-[3-(4-tert-butylbenzoyl)propyl]-piperidine were prepared as follows:

| | |
|---|---|
| 4-diphenylmethoxy-1-[3-(4-tert-butylbenzoyl)propyl]-piperidine | 750 g. |
| lactic acid | 6250 g. |
| glycerin | 4500 g. |
| hydrogenated castor oil-ethylene oxide | 3000 g. |
| sodium methyl p-hydroxybenzoate | 240 g. |
| sodium propyl p-hydroxybenzoate | 60 g. |
| sodium saccharin | 300 g. |
| flavouring | q.s. |
| sodium hydroxide q.s. | pH = 4 |
| demineralised water q.s. | 150 liters |

Procedure

To a solution of the sodium methyl (and propyl) p-hydroxybenzoates and sodium saccharin in 30 liters of demineralised water, an aqueous glycerin solution of lactic acid and hydrogenated castor oil-ethylene oxide was added. After stirring, the 4-diphenylmethoxy-1-[3-(4-tert-butylbenzoyl)-propyl]-piperidine was added and homogenized to reach complete dissolution. After this, the flavouring agent was mixed into the solution with vigorous stirring, and the mixture was made up to final volume with demineralised water.

The resultant solution was filled into 150 ml bottles using an appropriate filling machine.

EXAMPLE 8

50,000 capsules each containing 50 mg of 4-diphenylmethoxy-1-[3-(4-tert-butylbenzoyl)propyl]-piperidine were prepared from the following formulation:

| | |
|---|---|
| 4-di-phenylmethoxy-1-[3-(4-tert-butylbenzoyl)-propyl]-piperidine | 2,500 g |
| magnesium stearate | 5,000 g |
| lactose spray dried | 11,175 g |
| Pluronic F-68 ("Pluronic" is a registered Trade Mark) | 2,000 |
| sodium lauryl sulphate | 1,750 g |

Procedure

The 4-dipheenylmethoxy-1-[3-(4-tert-butylbenzoyl)-propyl]-piperidine, sodium lauryl sulphate, lactose and Pluronic F-68 were mixed together and passed through a screen with an opening of 0.6 mm. The magnesium stearate was added and the mixture encapsulated into gelatine capsules of appropriate size.

EXAMPLE 9

100,000 tablets each containing 25 mg of 4-diphenylmethoxy-1-[3-(4-tert-butylbenzoyl)propyl]-piperidine were prepared from the following formulation:

| | |
|---|---|
| 4-diphenylmethoxy-1-[3-(4-tert-butylbenzoyl)propyl]-piperidine | 2,500 g |
| microcrystalline cellulose | 1,650 g |
| lactose spray dried | 9,620 g |
| carboxymethyl starch | 570 g |
| sodium stearyl fumarate | 80 g |
| colloidal silicon dioxide | 80 g |

Procedure

All the powders were passed through a screen with apertures of 0.6 mm. They were then all mixed in a suitable mixer for 30 minutes and compressed into 145 mg tablets using 6 mm discs and flat bevelled punches. The disintegration time of the tablets was about 60 seconds.

EXAMPLE 10

10,000 suppositories each containing 80 mg of 4-diphenylmethoxy-1-[3-(4-tert-butylbenzoyl)propyl]-piperidine were prepared as follows:

| | |
|---|---|
| 4-diphenylmethoxy-1-[3-(4-tert-butylbenzoyl)propyl]-piperidine | 800 g. |
| theobroma oil | 19,200 g. |

Procedure

The theobroma oil was melted and the active compound suspended in it. The mixture was then poured into appropriate suppository moulds to make 2.0 g suppositories.

We claim:

1. A compound of the formula I:

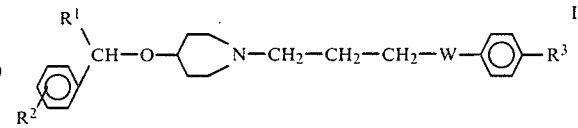

wherein $R^1$ represents a thienyl group, or a phenyl group optionally substituted by a halogen (preferably fluorine or chlorine) atom, a lower alkoxy or lower alkyl group, $R^2$ represents a hydrogen or halogen (preferably fluorine) atom, a lower alkoxy or lower alkyl group, $R^3$ represents a hydrogen or halogen (preferably fluorine) atom, a lower alkylthio, lower alkoxy or lower alkyl group, or a cycloalkyl group containing 5 or 6 carbon atoms, or a group of the formula:

wherein $R^4$ and $R^5$ singly each represents a hydrogen atom or lower alkyl group, $R^6$ represents a cycloalkyl containing 3 to 6 carbon atoms, hydroxymethyl, carboxy or lower alkoxycarbonyl group, and W represents a carbonyl

or a hydroxymethylene [viz. —CH(OH)—] group, and pharmacologically acceptable salts thereof.

2. A compound according to claim 1 wherein $R^1$ is a phenyl, fluorophenyl, methylphenyl, methoxyphenyl or thienyl group.

3. A compound according to claim 1 wherein $R^2$ is H, F, Cl, $CH_3$ or $CH_3O$.

4. A compound according to claim 1, wherein $R^3$ is H, F, Br, ethyl, isopropyl, tert-butyl, methoxy or cyclohexyl.

5. A compound according to claim 1, wherein $R^3$ is

where $R^4$ and $R^5$ are H or methyl and $R^6$ is cyclopropyl, ethoxycarbonyl, carboxy or hydroxymethyl.

6. A compound according to claim 1 in the form of an acid addition salt with fumaric acid.

7. A compound according to claim 1 which is 4-diphenylmethoxy-α-(4-tert-butylphenyl)-1-piperidinebutanol, 4-di-(4-fluorophenyl)methoxy-1-[3-(4-tert-butylbenzoyl)propyl]-piperidine, 4-[α-(2-thienyl)benzyloxy]-1-[3-(4-tert-butylbenzoyl)propyl]-piperidine, 4-diphenylmethoxy-α-(4-cyclohexylphenyl)-1-piperidine butanol and 4-diphenylmethoxy-1-[3-(4-isopropylbenzoyl)propyl]-piperidine and acid addition salts thereof.

8. A compound according to claim 1 which is 4-diphenylmethoxy-1-[3-(4-tert-butylbenzoyl)propyl]-piperidine and acid addition salts thereof.

9. A pharmaceutical composition useful for the treatment of symptoms of respiratory, allergic or cardiovascular disease states comprising an effective amount of a compound or salt according to claim 1 together with a pharmaceutically acceptable carrier or diluent.

10. A method for the treatment of symptoms of respiratory, allergic or cardiovascular disease states in a host which comprises administering to the host an effective amount of a compound or salt according to claim 1.

* * * * *